(12) United States Patent
Waldstreicher et al.

(10) Patent No.: US 6,268,377 B1
(45) Date of Patent: Jul. 31, 2001

(54) METHOD FOR TREATING ANDROGEN-RELATED CONDITIONS

(75) Inventors: Joanne Waldstreicher, Scotch Plains; Daniel Z. Wang, Edison, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/401,135

(22) Filed: Sep. 22, 1999

Related U.S. Application Data (60) Provisional application No. 60/102,018, filed on Sep. 28, 1998.

(51) Int. Cl.$^7$ .................. A61K 31/435; A61K 31/44
(52) U.S. Cl. .................. 514/284; 514/356; 514/15; 514/47; 514/170; 514/277; 514/279; 514/290; 514/298; 514/408; 514/412; 514/415; 514/354; 514/355
(58) Field of Search .................. 514/284, 356, 514/15, 47, 170, 277, 279, 290, 298, 408, 412, 415, 354, 355

(56) References Cited

U.S. PATENT DOCUMENTS

| | | |
|---|---|---|
| 3,267,104 | 8/1966 | Hermans et al. . |
| 3,485,847 | 12/1969 | Bossert et al. . |
| 3,562,257 | 2/1971 | Kugita et al. . |
| 4,115,432 | 9/1978 | Dengel . |
| 4,377,584 | 3/1983 | Rasmusson et al. . |
| 4,552,695 | 11/1985 | Igarashi et al. . |
| 4,593,042 | 6/1986 | Liang . |
| 4,681,970 | 7/1987 | Liang . |
| 4,760,071 | 7/1988 | Rasmusson et al. . |
| 4,906,646 * | 3/1990 | Honn et al. .................. 514/356 |
| 4,981,871 | 1/1991 | Abelson . |
| 5,525,601 | 6/1996 | Belmonte-Martinez et al. . |
| 5,641,500 | 6/1997 | Trepel et al. . |
| 5,698,549 | 12/1997 | Steers et al. . |
| 5,719,158 | 2/1998 | Durette et al. . |
| 5,756,480 | 5/1998 | Bull et al. . |
| 5,777,134 | 7/1998 | Bakshi et al. . |
| 5,886,012 * | 3/1999 | Pang et al. .................. 514/356 |
| 5,942,517 | 8/1999 | Nagarathnam et al. . |

FOREIGN PATENT DOCUMENTS

| | | | |
|---|---|---|---|
| 0285383 A2 | * | 5/1988 | (EP) . |
| 0459666A2 | * | 4/1991 | (EP) . |
| WO 91/00731 | * | 1/1991 | (WO) . |

OTHER PUBLICATIONS

Fischhof et al., Drugs of Today, vol. 29 (1993), pp. 57–95, "Senile dementia and calcium channel blockers: A review".

Rahwan et al., Annual Reports in Med. Chem., vol. 16 (1981), Chap. 23, "Calcium antagonists", pp. 257–268.

(List continued on next page.)

*Primary Examiner*—Zohreh Fay
*Assistant Examiner*—Brian-Yong Kwon
(74) *Attorney, Agent, or Firm*—Catherine D. Fitch; Philippe L. Durette; Melvin Winokur (57) ABSTRACT

The present invention provides for the combined use of 5α-reductase inhibitors together with calcium channel blockers for the treatment of benign prostatic hyperplasia (BPH), prostate cancer, prostatitis, hematuria, and other androgen related disorders, including prostatitis and the prevention of prostate cancer. This invention provides a method of treatment which is useful in the treatment of benign prostatic hyperplasia, prostatitis, and/or the prevention and treatment of prostatic cancer, as well as in the treatment of prostatitis and hematuria. This invention also provides a pharmaceutical composition which is useful in the treatment of benign prostatic hyperplasia, prostatitis, hematuria and/or the prevention and treatment of prostatic cancer, wherein the pharmaceutical composition comprises the combination of a 5α-reductase inhibitor and a calcium channel blocking agent.

19 Claims, 2 Drawing Sheets

OTHER PUBLICATIONS

Vanhoute et al., TIPS, vol. 8 (1987), "The WHO classification of Calcium antagonists", pp. 4–5.

Fleckenstein, Bayer Symposium IX, Cardiovascular effects of dihydropyridine–type calcium antagonists and agonists, "Calcium antagonists and calcium agonists: Fundamental criteria and classification", Fleckenstein et al., editors, Springer Verlag: Berlin Heidelberg (1985), pp. 3–31.

Meyer, Annual Reports in Med. Chem., vol. 17 (1982), Chap. 8, "Antianginal and anti–ischemic agents", pp. 71–77.

Meyer et al., Annual Reports in Med. Chem., vol. 18 (1983), Chap. 9, "Calcium antagonist—new opportunities", pp. 79–88.

* cited by examiner

METHOD FOR TREATING ANDROGEN-RELATED CONDITIONS

CROSS REFERENCE TO RELATED APPLICATIONS

The present application claims priority of U.S. provisional application Ser. No. 60/102,018, filed Sep. 28, 1998.

BACKGROUND OF THE INVENTION

Diseases of the prostate, including benign prostatic hyperplasia, prostatic cancer, and prostatitis may be related to hyperandrogenic stimulation caused by an excessive accumulation of testosterone ("T") or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in the prostate is 5α-dihydrotestosterone ("DHT"), formed locally in the prostate by the action of testosterone-5α-reductase (or simply 5α-reductase). Inhibitors of 5α-reductase will serve to prevent or lessen symptoms of hyperandrogenic stimulation in the prostate. See especially U.S. Pat. No. 4,377,584, issued Mar. 22, 1983, and U.S. Pat. No. 4,760,071, issued Jul. 26, 1988, both assigned to Merck & Co., Inc.

The enzyme 5α-reductase catalyzes the reduction of testosterone to the more potent androgen, dihydrotestosterone, as shown below:

Finasteride, (17β-(N-tert-butylcarbamoyl)-3-oxo-4-aza-5α-androst-1-ene-3-one) as shown below, is a potent inhibitor of the human prostate enzyme.

finasteride

Under the trade name PROSCAR®, finasteride is known to be useful in the treatment of hyperandrogenic conditions; see eg. U.S. Pat. No. 4,760,071. Finasteride is currently prescribed for the treatment of benign prostatic hyperplasia (BPH), a condition afflicting to some degree the majority of men over age 55. Under the trade name PROPECIA®, a lower dose of finasteride is prescribed for the treatment of male pattern hair loss. Finasteride's utility in the treatment of androgenic alopecia and prostatic carcinoma is also disclosed in the following documents: EP 0 285,382, published Oct. 5, 1988; EP 0 285,383, published Oct. 5, 1988.

There are two isozymes of 5α-reductase in humans. One isozyme (type 1 or 5α-reductase 1) predominates in sebaceous glands of facial and skin tissue and is relatively insensitive to finasteride (see, e.g., G. Harris, et al., *Proc. Natl. Acad. Sci. USA*, Vol. 89, pp. 10787–10791 (November 1992)); the other (type 2 or 5α-reductase 2) predominates in the prostate and is potently inhibited by finasteride. A genus of 16β-substituted-4-azasteroids are described in U.S. Pat. No. 5,719,158.

Calcium channel blockers such as nifedipine, verapamil and diltiazem, are used in the treatment of cardiovascular diseases. Calcium channel blockers or antagonists are compounds which delay or prevent the cardiac contracture which is believed to be caused by an accumulation of intracellular calcium under ischemic conditions. Calcium overload, during ischemia, can have a number of additional adverse effects which would further compromise the ischemic myocardium. These include less efficient use of oxygen for ATP production, activation of mitochondrial fatty acid oxidation, and possibly, promotion of cell necrosis. Thus, calcium channel blockers are useful in the treatment or prevention of cardiac conditions, such as angina pectoris, cardiac arrhythmias, heart attacks and cardiac hypertropy. Calcium channel blockers also possess vasodilator activity and are thus useful as antihypertensives and for the treatment of coronary vasospasm. Calcium channel blockers of the verapamil type are known to lower elevated intraocular pressure. See U.S. Pat. No. 4,981,871. Calcium channel blockers are not suggested as useful for treating androgen-related conditions, including benign prostatic hyperplasia.

SUMMARY OF THE INVENTION

The present invention provides for the combined use of 5α-reductase inhibitors together with calcium channel blockers for the treatment of benign prostatic hyperplasia (BPH), prostate cancer, prostatitis, hematuria, and other androgen related disorders, including androgenetic alopecia. It is an object of this invention to provide a method of treatment which is useful in the treatment of benign prostatic hyperplasia, prostatitis, hematuria and/or the prevention and treatment of prostatic cancer. It is also an object of this invention to provide a pharmaceutical composition which is useful in the treatment of benign prostatic hyperplasia, prostatitis, hematuria and/or the prevention and treatment of prostatic cancer, wherein the pharmaceutical composition comprises the combination of a 5α-reductase inhibitor and a calcium channel blocking agent.

DETAILED DESCRIPTION OF THE INVENTION

Among the 5α-reductase inhibiting compounds useful in the method of treatment of benign prostatic hyperplasia, prostatitis, hematuria and/or the prevention and treatment of prostatic cancer, are the compounds of structural formula I:

wherein R is selected from:
(a) $C_{1-10}$ alkyl, unsubstituted or substituted with one to three halogen substituents,
(b) phenyl, unsubstituted or substituted with one to three substituents independently selected from halogen, methyl, and trifluoromethyl
(c) benzyl, unsubstituted or substituted on the methylene or phenyl group with one to three substituents independently selected from halogen, methyl and trifluoro methyl.

In one embodiment of compounds of structural formula I, R is selected from:
(a) unsubstituted $C_{1-10}$ alkyl,
(b) phenyl unsubstituted or substituted with one or two trifluoromethyl substituents
(c) benzyl, unsubstituted or substituted on the methylene with one or two trifluoromethyl substituents.

In another embodiment of compounds of structural formula I, R is t-butyl.

In yet another embodiment of compounds of structural formula I, R is 2,5-bis(trifluoromethyl)phenyl.

In still another embodiment of compounds of structural formula I, R is

Other inhibitors of 5α-reductase useful in the methods and compositions of the present invention include epristeride, turosteride, LY300502, and FK-143, shown below:

epristeride turosteride

LY300502

FK143

Calcium Channel Blockers (CCBs) have been known for years to be useful agents in the treatment of ischemic heart disease. Calcium channel blockers useful in the present invention can be generally divided into three structural classes: dihydropyridines, such as nicardipine and nifedipine; arylalkylamines, such as verapamil; and benzothiazepines, such as diltiazem.

The dihydropyridine class of calcium channel blockers may be represented by structural formula II:

(II)

$R^1$ is selected from $C_{1-6}$ alkyl- and $C_{1-6}$ alkyloxy-$C_{1-6}$ alkyl-. In one embodiment, $R^1$ is selected from $C_{1-3}$ alkyl; $C_{1-6}$ alkyloxy-$C_{1-2}$ alkyl-. In another embodiment of the present invention, $R^1$ is selected from methyl, ethyl, isopropyl, isobutyl and n-propyloxyethyl-.

$R^2$ is selected from: $C_{1-6}$alkyl-, $C_{1-6}$ alkyloxy-$C_{1-6}$ alkyl-, $N(R^4)_2$-$C_{1-6}$ alkyl-O-$C_{1-6}$ alkyl-; and aryl-$C_{1-6}$ alkyl-N($R^4$)-$C_{1-6}$ alkyl. In one embodiment of the present invention, $R^2$ is selected from $C_{1-4}$ alkyl, $C_{1-6}$ alkyloxy-$C_{1-2}$ alkyl-, phenyl-$C_{1-2}$ alkyl-N($R^4$)-$C_{1-6}$ alkyl.

$R^3$ is selected from hydrogen and hydroxy. In one embodiment of the present invention, $R^3$ is hydrogen. In another embodiment of the present invention, $R^3$ is is hydroxy.

$R^4$ is selected from hydrogen, methyl and ethyl. In one embodiment of the present invention, $R^4$ is methyl.

$R^5$ is selected from hydrogen and heterocyclo-$C_{1-3}$ alkyl. In one embodiment of the present invention, $R^5$ is selected from hydrogen and 2-(4-morpholinyl)-ethyl-. In another embodiment of the present invention, $R^5$ is hydrogen.

X is selected from —$NO_2$, trifluoromethyl, 1,1-difluoromethoxy, methoxy, and halogen. In one embodiment of the present invention, X is selected from —$NO_2$, 1,1-difluoromethoxy and chloro. In another embodiment of the present invention, X is selected from —$NO_2$ and chloro. In yet another embodiment of the present invention, X is chloro.

Y is selected from hydrogen and halogen. In one embodiment of the present invention, Y is selected from hydrogen and chloro. In another embodiment of the present invention, Y is hydrogen.

Alternatively, X, Y and the phenyl ring to which they are attached are combined to form a benzoxadiazolyl ring.

Nifedipine (1,4-dihydro-2,6-dimethyl4-(2-nitrophenyl)-3,5-pyridine dicarboxylic acid dimethyl ester) is disclosed in U.S. Pat. No. 3,485,847. Similar compounds to nifedipine are disclosed in U.S. Pat. Nos. 3,455,945; 3,325,505; 3,441,468; 3,470,297 and 3,511,837. Other pyridine compounds having calcium channel blocking activity are disclosed in U.S. Pat. Nos. 3,799,934; 4,154,839; 4,264,611; 4,466,972; 4,652,573; 4,755,512; 4,791,117; 4,794,187; 4,814,455; 4,829,076; 4,871,745; 4,895,846; and 4,912,223.

Calcium channel blockers of structural formula II also include:

Nicardipine (1,4-dihydro-2,6-dimethyl-4-(2-nitrophenyl)-3,5-pyridine dicarboxylic acid methyl 2-(methyl-(phenylmethyl) amino) ethyl ester); Nitrendipine (1,4-dihydro-2,6-dimethyl-4-(3-nitrophenyl)-3,5-phyridindicarboxylic acid ethyl methyl ester); Nisoldipine (1,4-dihydro-2,6-dimethyl-4-(2-nitrophenyl)-3,5- pyridinedicarboxylic acid methyl 2-methylpropyl ester); Felodipine (4-(2,3-dichlorophenyl)-1,4dihydro-2,6-dimethyl-3,5-pyridinedicarboxylic acid ethyl methyl ester); Nimodipine (1,4-dihydro-2,6dimethyl-4-(3-nitrophenyl-3,5-pyridinedicarboxylic acid 2-methoxyethyl 1-methylethyl ester); Niludipine; Amlodipine (2-((2-aminoethoxy) methyl)-4-(2-chlorophenyl)-1,4-dihydro-6-methyl-3,5-pyridinedicarboxylic acid 3-ethyl 5-methyl ester); Flordipine; Ryosidine; FR 7534; Nilvadipine (FR 34235, 2-cyano-1,4-dihydro-6-methyl-4-(3-nitrophenyl)-3,5-pyridinedicarboxylic acid 3-methyl 5-(1-methylethyl) ester); PY 108-068; and Isradipine (PN 200-110, 4-(4-benxofurazanyl)-1,4-dihydro-2,6-dimethyl-3,5-pyridinedicarboxylic acid methyl 1-methyl-ethyl ester).

Representatives of the arylalkylamine class of calcium channel blockers may be represented by structural formula III:

(III)

$R^6$ is selected from hydrogen, methoxy, hydroxy, and halogen. In one embodiment of the present invention, $R^6$ is selected from hydrogen and methoxy.

$R^7$ is selected from hydrogen, $C_{1-5}$ alkyl, saturated or unsaturated $C_{3-6}$ cycloalkyl, benzyl and phenyl. In one embodiment of the present invention, $R^7$ is isopropyl.

$R^8$ is cyano.

Alternatively, $R^7$ and $R^8$ may together form the following: —$SO_2(CH_2)_3SO_2$—.

Verapamil, 5-((3,4-dimethoxyphenethyl)methylamino)-2-(3,4-dimethoxyphenyl)-2-isopropylvaleronitrile, and other closely related phenylalkylamine calcium channel blockers are disclosed in U.S. Pat. Nos. 3,261,859; 4,593,042 and 4,681,970. Gallopamil, 5-((3,4-dimethoxyphenethyl) methylamino)-2-isopropyl-2-(3,4,5-trimethoxyphenyl) valeronitrile, is disclosed in U.S Pat. No. 3,261,859; 4,115,432.

Certain arylalkylamine calcium channel blockers are represented by structural formula (VI):

(VI)

$R^{14}$ is selected from phenyl and benzyl. Prenylamine, N-(1-methyl-2-phenylethyl-γ-phenylbenzene propanamine, and related compounds are disclosed in U.S. Pat. No. 3,152,173. Fendiline, N-(1-phenylethyl)-3,3-diphenyl propylamine, and related compounds are disclosed in U.S. Pat. 3,262,977.

Another arylalkylamine calcium channel blocker is terodiline, 4,4-diphenyl-2-(tert-butylamino)butane, which, along with related compounds, is disclosed in U.S. Pat. No. 3,371,014.

Yet another arylalkylamine calcium channel blocker is bepridil, β-((2-methylpropoxy)methyl)-N-phenyl-N-(phenylmethyl)-1-pyrrolidineethanamine, which is disclosed in U.S. Pat. No. 3,962,238, along with related compounds.

The arylalkylamino calcium channel blocker terbutaline, 5-(2-((1,1-dimethylethyl)amino)-1-hydroxyethyl)-1,3-benzenediol, is disclosed in U.S. Pat. No. 3,937,838.

Amiloride, 3,5-diamino-N-(aminoiminomethyl)-6-chloropyrazinecarboxamide, and related componds are disclosed in Belgian patent 639,386.

Bencyclane, N,N-dimethyl-3-((1-(phenylmehtyl)-cycloheptyl)oxy)-1-propanamine is a calcium channel blocker disclosed in Hungarian Pat. 151,865.

Etafenone, 1-(2-(2-(diethylamino)ethoxy)phenyl)-3-phenyl-1-propanone is a calcium channel blocker disclosed in German patent 1,265,758.

Benzothiazepine calcium channel blockers are represented by structural formula IV:

(IV)

$R^9$ is a phenyl group either unsubstituted or substituted with 1 to 3 substituents independently selected from $C_{1-8}$ alkyl, $C_{1-8}$ alkyloxy, and halogen. In one embodiment of the present invention, $R^9$ is a phenyl group either unsubstituted or substituted with 1 to 3 substituents selected from methyl, ethyl, propyl, isopropyl, butyl, methoxy, ethoxy, propoxy, isopropoxy, and butoxy. In another embodiment of the present invention, $R^9$ is selected from phenyl, either unsubstituted or substituted with a substituent selected from methyl, methoxy, and chloro. In still another embodiment of the present invention, $R^9$ is selected from 4-methylphenyl, 4-methoxyphenyl, 4-chlorophenyl. In one class of this embodiment, $R^9$ is 4-methoxyphenyl.

$R^{10}$ is selected from hydrogen and $C_{2-8}$ alkanoyl. In one embodiment of the present invention, $R^{10}$ is selected from hydrogen, acetyl, propionyl and butyryl. In another embodiment of the present invention, $R^{10}$ is acetyl. In still another embodiment of the present invention, $R^{10}$ is hydrogen.

$R^{11}$ and $R^{12}$ are each independently selected from $C_{1-8}$ alkyl. In one embodiment of the present invention, $R^{11}$ and $R^{12}$ are independently selected from methyl, ethyl, propyl, isopropyl, and butyl. In one class of the present invention, $R^{11}$ and $R^{12}$ are each methyl.

$X^1$ is selected from hydrogen and halogen. In one embodiment of the present invention $X^1$ is selected from hydrogen, chloro-, and bromo-. In one class of the presnt invention, $X^1$ is hydrogen.

$Y^1$ is an alkylene group of 2 or 3 carbon atoms. In one embodiment of the present invention, $Y^1$ is —$CH_2$—$CH_2$—.

Diltiazem and the like are disclosed in U.S. Pat. Nos 3,562,257 and 4,552,695.

Piperazinyl calcium channel blockers are represented by structural formula V:

(V)

$R^{13}$ is independently selected from hydrogen and halogen at each occurrence. In one embodiment of the present invention, $R^{13}$ selected from hydrogen and fluorine. In another embodiment of the present invention, each $R^{13}$ is hydrogen. In still another embodiment of the present invention, each $R^{13}$ is fluoro.

Flunarizine, (E)-1-(bis(4-fluorophenyl)methyl)-4-(3-phenyl-2-propenyl)piperazine, is disclosed in U.S. Pat. No. 3,773,939. Cinnarizine, 1-diphenylmethyl)-4-(3-phenyl-2-propenyl)piperazine is disclosed in U.S. Pat. No. 2,882,271.

Another piperazinyl calcium channel blocker, lidoflazine, 4-(4,4-bis(4-fluorophenyl)butyl)-N-(2,6-dimethylphenyl)-1-piperazineacetamide, and related compounds are disclosed in U.S. Pat. No. 3,267,104.

The piperadinyl calcium channel blocker, perhexiline, 2-(2,2-dicyclohexylethyl)piperidine, and related compounds are disclosed in British Patent 1,025,578.

Mibefradil, (1S,2S)-2-(2-((3-2-benzimidazolyl)propyl) methylamino)ethyl)-6-fluoro-1,2,3,4-tetrahydro-1-isopropyl-2-naphthyl methoxyacetate is disclosed in U.S. Pat. No. 4,808,605.

In addition, lanthanum ($La^{3+}$, $La_2O_3$) is used as a specific antagonist of calcium in experimental biology.

In structural formulae I, II, III, IV, V and VI, combinations of substituents and/or variables are permissible only if such combinations result in stable compounds.

The term "halo" or "halogen" is meant to include fluoro, chloro, bromo and iodo.

The term "$C_{1-10}$ alkyl" and the like is meant to include both straight-and branched-chain alkyl groups of the specified number of carbon atoms in length, not limited to: methyl, ethyl, propyl, butyl, pentyl, hexyl, heptyl, octyl, nonanyl, decyl and the isomers thereof such as isopropyl, isobutyl, secbutyl, t-butyl, isopentane, isohexane, etc., depending on the number of carbon atoms specified.

The term heterocycle or heterocyclic, as used herein except where noted, represents a stable 5- to 7-membered mono- or bicyclic or stable 7- to 10-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, benzoxadiazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Especially preferred are morpholinyl and benzoxadiazolyl.

Many organic compounds can form complexes with solvents in which they are reacted or from which they are precipitated or crystallized. These complexes are known as "solvates". Solvates of compounds of structural formulae I–IV are within the scope of the present invention. Many organic compounds can exist in more than one crystalline form. For example, crystalline form may vary from solvate to solvate. Thus, all crystalline forms of the compounds of structural formula I or the pharmaceutically acceptable solvates thereof are within the scope of the present invention.

Some of the crystalline forms for compounds of the present invention may exist as polymorphs and as such are intended to be included in the present invention.

The term "therapeutically effective amount" shall mean that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated.

This listing above represents primarily the well-known calcium channel blocking agents, i.e, those marketed or tested for human use. But the mere listing of these particular, presently marketed or tested calcium channel blocking agents is not intended to limit the scope of the compounds which might be used in practicing the present invention. Any calcium channel blocking argent can be used in accordance with this invention.

Accordingly, the present invention has the objective of providing methods of treating androgen related conditions comprising the oral, systemic, parenteral or topical administration to a subject in need of such treatement of a therapeutically effective amount of a 5α-reductase inhibitor in combination with a calcium channel blocking agent. In particular, the present invention provides for the treatment of the conditions of benign prostatic hyperplasia, prostatitis, hematuria and/or the prevention and treatment of prostatic cancer, comprising the administration to a subject in need of such treatment of a 5α-reductase inhibitor in combination with a calcium channel blocking agent.

The present invention also has a further objective of providing methods of treating androgen-related disorders such as: benign prostatic hyperplasia, prostatitis and the preventing and/or treating of prostatic cancer, by oral, systemic, parental or topical administration of a combined therapy of a therapeutically effective amount of a 5α-reductase inhibitor and a calcium channel blocker together with a therapeutically effective amount of an anti-androgen, such as, e.g., flutamide, spironolactone or casodex.

For the combination treatment of the present invention, where the active agents are in separate dosage formulations, the active agents can be administered concomitantly, or they each can be administered at separately staggered times.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The compounds usefull in the present invention, including the compounds of structural formulae I–VI useful in the present invention are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices may be administered systemically, by oral administration or by intravenous or intramuscular injection or topically.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing the active compound of the present invention with lactose and magnesium stearate, calcium stearate, starch, talc, or other carriers, and placing the mixture in gelatin capsules.

Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamide-phenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds for the present invention can be administered in intranasal form via topical use of suitable intmnasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

Preferably, doses of the compound of structural formula I useful in the method of the present invention range from 0.01 to 1000 mg per adult human per day. Most preferably, dosages range from 0.1 to 50 mg/day. For oral administration, the compositions are preferably provided in the form of tablets containing 0.01 to 1000 milligrams of the active 5α-reductase inhibiting ingredient, particularly 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Calcium channel blocking activity varies substantially from compound to compound. Generally, when administered systemically, calcium channel blocking agents are effective in a wide range of concentrations. For example, diltiazem tablets contain 30 to 120 mg of active per tablet. Preferably, doses of the calcium channel blockers useful in the method of the present invention range from 0.1 to 1000 mg per adult human per day. Most preferably, dosages range from 1.0 to 50 mg/day. For oral administration, the compositions are preferably provided in the form of tablets containing 0.01 to 1000 milligrams of the active calcium channel blocker, particularly 1.0, 2.0, 3.0, 5.0, 10.0, 15.0, 20.0, 25.0, 30.0, 40.0, 50.0, 60.0, 70.0, 80.0, 90.0 100.0, 110.0, 120.0, 130.0, 140.0, 150.0, 160.0, 170.0, 180.0, 190.0, 200.0, 225.0, 250.0, 275.0, 300.0, 325.0, 350.0, 375.0, 400.0, 425.0, 450.0, 475.0, and 500.0 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in divided doses of two, three or four times daily.

The compounds of the present invention may be used in the preparation of a medicament useful for the treatment of disorders including: benign prostatic hyperplasia, prostatitis, hematuria and prostatic cancer. For the treatment of hyperandrogenic conditions, the 5α-reductase inhibitors and calcium channel blocking agents may be combined in a single oral, topical, systemic or parenteral dosage formulation. Alternatively, a combined therapy can be employed wherein the 5α-reductase inhibitor and the calcium channel blocking agent are administered in separate oral, systemic, or parenteral dosage formulations. For example, a 5α-reductase inhibiting compound and a calcium channel blocking agent can be administered in a single oral or topical dosage formulation, or each active agent can be administered in a separate dosage formulation, e.g., in separate oral dosage formulations, or an oral dosage formulation of the 5α-reductase inhibitor in combination with a topical dosage formulation of the calcium channel blocker.

Also, for the treatment of benign prostatic hyperplasia, a combined therapy comprising a administration of a 5α-reductase inhibitor, such as e.g., finasteride, a calcium channel blocking agent, such as e.g., nifedipine, and an alpha-1 adrenergic receptor antagonist, such as e.g., terazosin, doxazosin, prazosin, bunazosin, indoramin or alfuzosin, may be employed. More particularly, the combined therapy can comprise administering a 5α-reductase inhibitor, a calcium channel blocking agent, and an alpha-$1_a$ adrenergic receptor antagonist (formerly called an alpha-$1_c$ adrenergic receptor antagonist). Compounds which are useful as alpha-$1_a$ adrenergic receptor antagonists can be identified according to procedures known to those of ordinary skill in the art, for example, as described in U.S. Pat. No. 5,403,847.

Also, for the treatment of hyperandrogenic conditions generally, and benign prostatic hyperplasia in particular, combined therapy comprising administration of a 5α-reductase inhibitor, such as e.g., finasteride, a calcium channel blocking agent, such as e.g., nifedipine, and an antiandrogen such as e.g., flutamide, spironolactone or casodex.

For the combination treatment of the present invention where the active agents are in separate dosage formulations, the active agents can be administered concurrently, or they each can be administered at separately staggered times.

The following examples are provided to further illustrate details for the preparation of the compound of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

EXAMPLE 1

Effect of Concomitant Use of Calcium Channel Blocker and 5α-Reductase Inhibitor

A total of 3040 men with clinical benign prostatic hyperplasia (BPH) diagnosed on the basis of moderate-to-severe symptoms, a decreased peak urinary flow rate (less than 15 mL/sec with a voided volume of 150 mL or more) and an enlarged prostate gland by digital rectal examination (DRE) were enrolled in a four-year study comparing finasteride with placebo. Men receiving alpha blocking agents or antiandrogens, and men with a history of chronic prostatitis, recurrent urinary tract infections, prostate or bladder cancer or surgery, or a serum prostate specific antigen (PSA) over 10 ng/mL were excluded. Men with serum PSA concentrations between 4.0 and 9.9 ng/mL had to have a negative prostate biopsy prior to enrollment.

After a one-month single-blind placebo lead-in, men were randomly assigned to receive placebo or 5 mg of finasteride (17β-(N-tert-butylcarbamoyl)-3-oxo-4-aza-5α-androst-1-en-3-one) daily in a four year, double-blind placebo-controlled study. BPH-related outcomes including symptoms, bothersomeness, adverse events and urinary flow rates, were assessed every 4 months. Serum PSA was measured every 4 months in the first year and then every 8 months at a central laboratory. Physical examination and routine hematological and serum chemistry tests were performed yearly. Magnetic resonance imaging (MRI) was performed at baseline and subsequently yearly in a subset of 10% of patients. All MRI images were read by a central radiologist blinded to treatment allocation and time of imaging.

Acute urinary retention (AUR) and surgery for BPH were predefined secondary end-points. The endpoint committee, blinded to treatment group, reviewed all study-related documents related to episodes of acute urinary retention, and all prostate surgeries for BPH, excluding surgery for prostate cancer. The endpoint committee classified episodes of AUR as spontaneous versus precipitated (when contributing factors such as urinary tract infection, surgery anesthesia, ingestion of alpha sympathomimetic drugs or anticholinergics were identified).

Complete data on outcomes, including four-year follow-up information for men who had discontinued treatment, were available for 92% of the men randomized. In the other 8%, complete information was available until discontinuation of the medication or up to the 6-month follow-up assessment after discontinuation.

The data were organized into three categories: (a) 2348 patients who did not take any calcium channel blocker during the study period; (b) 461 patients who took a calcium channel blocker more than 365 days during the study, and (c) 207 patients who took a calcium channel blocker less than 365 days during the study. For a relatively clean comparison, data from patients in categories (a) and (b) were analyzed and patients in category (c) were excluded.

As shown in FIGS. 1, 2, 3, and 4, the finasteride patients who took calcium channel blockers had a greater decrease in PSA, prostate volume and a greater increase in maximum urinary flow rate than the finasteride patients who did not take any calcium channel blocker. The placebo patients who took calcium channel blockers had a greater decrease in PSA and quasi-AUA score and greater increase in maximum urinary flow rate than the placebo patients who did not take any calcium channel blocker. The growth rate of prostate volume was about the same in both types of placebo patients.

Figure 1:
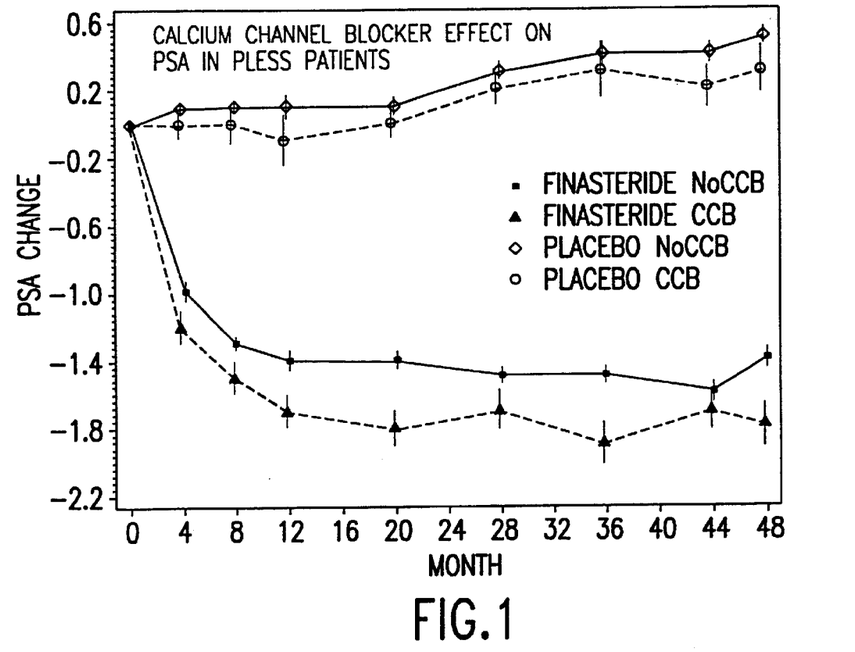
FIG. 1 is a graph of the effect of calcium channel blockers on PSA (prostate specific antigen) in ng/mL in patients enrolled in the clinical study detailed in Example 1, graphed as change of PSA versus time in the study (in months). The filled-in squares represent patients receiving finasteride only, the filled-in triangles represent the data from patients receiving both finasteride and a calcium channel blocker for more than 365 days. The open diamonds represent placebo patients receiving no calcium channel blocker and the open circles represent placebo patients receiving calcium channel blocker for more than 365 days. This graph shows that finasteride patients who received calcium channel blockers had the greatest decrease in PSA, greater than finasteride patients who did not take any calcium channel blockers and greater than the placebo patients and the placebo patients receiving calcium channel blockers.
Figure 2:
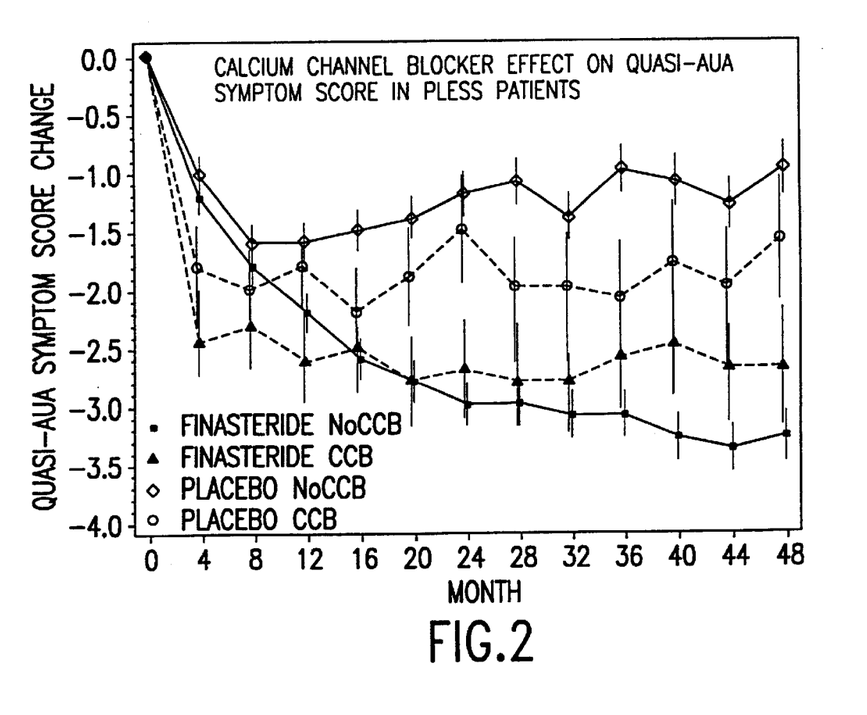
FIG. 2 is a graph of the effect of calcium channel blockers on the Quasi-AUA symptom score in patients enrolled in the clinical study detailed in Example 1, graphed as change in Quasi-AUA symptom score versus time in the study (in months). The filled-in squares represent patients receiving finasteride only, the filled-in triangles represent the data from patients receiving both finasteride and a calcium channel blocker for more than 365 days. The open diamonds represent placebo patients receiving no calcium channel blocker and the open circles represent placebo patients receiving calcium channel blocker for more than 365 days. This graph shows that finasteride patients who received calcium channel blockers had the greatest decrease in symptom score, greater than finasteride patients who did not take any calcium channel blockers and greater than the placebo patients and the placebo patients receiving calcium channel blockers.
Figure 3:
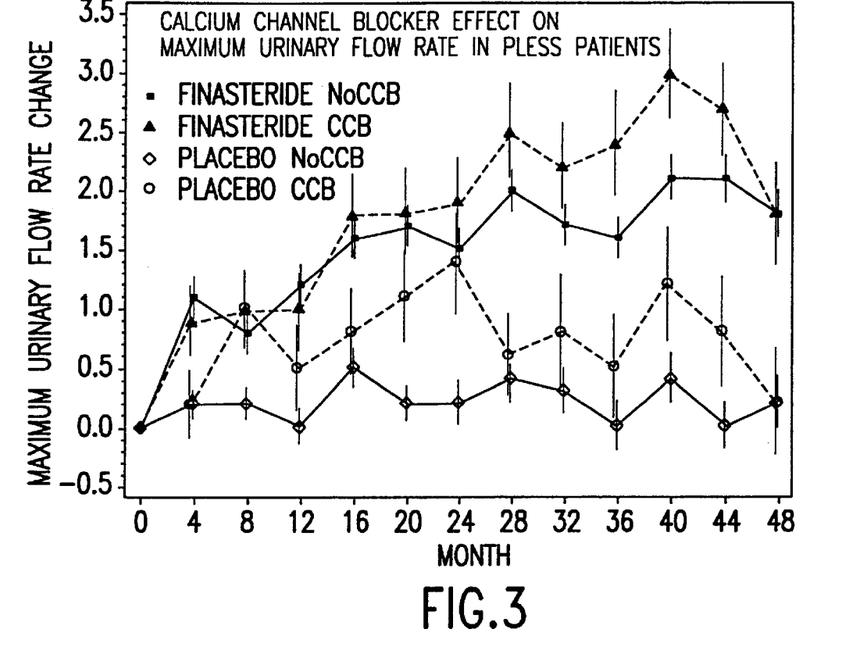
FIG. 3 is a graph of the effect of calcium channel blockers on the maximum urinary flow in patients enrolled in the clinical study detailed in Example 1, graphed as change maximum urinary flow rate (mL/sec) versus time in the study (in months). The filled-in squares represent patients receiving finasteride only, the filled-in triangles represent the data from patients receiving both finasteride and a calcium channel blocker for more than 365 days. The open diamonds represent placebo patients receiving no calcium channel blocker and the open circles represent placebo patients receiving calcium channel blocker for more than 365 days. This graph shows that finasteride patients who received calcium channel blockers had the greatest increase in maximum flow rate after 12 months, greater than finasteride patients who did not take any calcium channel blockers and greater than the placebo patients and the placebo patients receiving calcium channel blockers.
Figure 4:
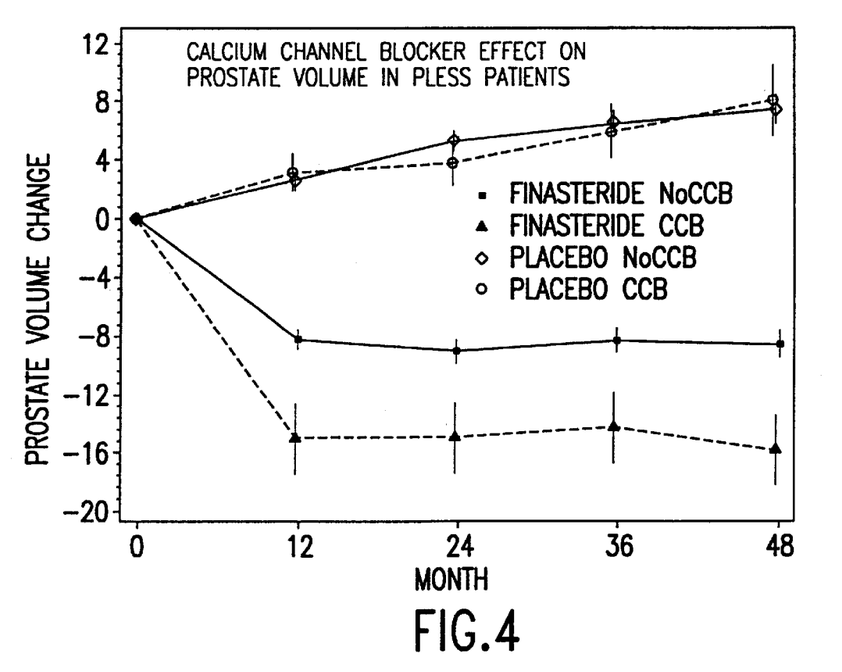
FIG. 4 is a graph of the effect of calcium channel blockers on prostate volume in patients enrolled in the clinical study detailed in Example 1, graphed as change in prostate volume ($cm^3$) versus time in the study (in months). The filled-in squares represent patients receiving finasteride only, the filled-in triangles represent the data from patients receiving both finasteride and a calcium channel blocker for more than 365 days. The open diamonds represent placebo patients receiving no calcium channel blocker and the open circles represent placebo patients receiving calcium channel blocker for more than 365 days. This graph shows that finasteride patients who received calcium channel blockers had the greatest decrease in prostate volume, greater than finasteride patients who did not take any calcium channel blockers and greater than the placebo patients and the placebo patients receiving calcium channel blockers.

Among the two types of finasteride patients, symptom score initally improved much faster for the patients with calcium channel blockers than those who did not take a calcium channel blocker, although by month 16, the rate of improvement in the finasteride only group continued to increase, whereas the finasteride plus calcium channel blocker group experienced a decreased rate of improvement in symptom score.

Tables 1 and 2 contain the incidence of urologic events in the calcium channel blocker and non-calcium channel blocker patient groups. The incidence of urologic surgery and the incidence of spontaneous acute urinary retention (AUR) were lower in both finasteride and placebo treated patients who were also on calcium channel blockers. The incidence of precipitated AUR was higher in both finasteride and placebo treated patients who were not on calcium channel blockers.

TABLE 1

Urologic Events in patients who took a calcium channel blocker for more than 365 days

|  | Finasteride (N = 236) | Placebo (N = 225) | Hazard Ratio (95% CI) |
| --- | --- | --- | --- |
| Surgery and AUR | 5.9% | 10.7% | 0.53 (0.28 to 1.00) |
| Surgery | 3.8% | 6.7% | 0.55 (0.25 to 1.22) |
| AUR | 3.0% | 6.2% | 0.46 (0.20 to 1.10) |
| Spontaneous AUR | 0.4% | 1.8% | 0.24 (0.05 to 1.21) |
| Precipitated AUR | 2.5% | 4.9% | 0.50 (0.19 to 1.31) |

TABLE 2

Urologic Events in patients who did not take a calcium channel blocker

|  | Finasteride (N = 1181) | Placebo (N = 1167) | Hazard Ratio (95% CI) |
| --- | --- | --- | --- |
| Surgery and AUR | 6.4% | 13.3% | 0.48 (0.37 to 0.62) |
| Surgery | 4.4% | 10.6% | 0.42 (0.31 to 0.57) |
| AUR | 2.6% | 6.2% | 0.44 (0.30 to 0.64) |
| Spontaneous AUR | 1.4% | 3.9% | 0.38 (0.23 to 0.62) |
| Precipitated AUR | 1.4% | 2.5% | 0.55 (0.31 to 0.99) |

EXAMPLE 12

Oral Composition

As a specific embodiment of an oral composition of a compound of this invention, 5 mg of finasteride and 10 mg of nifedipine are formulated with sufficient finely divided lactose to provide a total amount of 580 to 590 mg to fill a size 0 hard gelatin capsule.

Biological Assays

Preparation of Human Prostatic and Scalp 5α-reductases.

Samples of human tissue were pulverized using a freezer mill and homogenized in 40 mM potassium phosphate, pH 6.5, 5 mM magnesium sulfate, 25 mM potassium chloride, 1 mM phenylmethyl-sulfonyl fluoride, 1 mM dithiothreitol (DTT) containing 0.25 M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-Reductase Assay

The reaction mixture for the type 1 5α-reductase contained 40 mM potassium phosphate, pH 6.5, 5 $\mu$M [7-$^3$H]-testosterone, 1 mM dithiothreitol and 500 $\mu$M NADPH in a final volume of 100 $\mu$l. The reaction mixture for the type 2 5α-reductase contained 40 mM sodium citrate, pH 5.5, 0.3 $\mu$M [7-$^3$H]-testosterone, 1 mM dithiothreitol and 500 $\mu$M NADPH in a final volume of 100 $\mu$l. Typically, the assay was initiated by the addition of 50–100 $\mu$g prostatic homogenate or 75–200 $\mu$g scalp homogenate and incubated at 37° C. After 10–50 min the reaction was quenched by extraction with 250 $\mu$l of a mixture of 70% cyclohexane: 30% ethyl acetate containing 10 $\mu$g each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition Studies

Compounds were dissolved in 100% ethanol. $IC_{50}$ values represent the concentration of inhibitor required to decrease enzyme activity to 50% of the control. $IC_{50}$ values were determined using a 6 point titration where the concentration of the inhibitor was varied from 0.1 to 1000 nM.

Representative compounds of this invention were tested in the above desribed assay for 5α-reductase type 1 and type 2 inhibition. For the inhibition of 5α-reductase type 1, the compounds have $IC_{50}$ values lower than 600 nM, with the majority of compounds having $IC_{50}$ values ranging from about 0.3 nM to about 200 nM. For the inhibition of 5α-reductase type 2, the same compounds have $IC_{50}$ values greater than about 155 nM, with the majority of compounds having $IC_{50}$ values greater than 1000 nM. Each compound has at least a 2-fold greater selectivity for inhibition of 5α-reductase type 1 over type 2, with the majority of the compounds having a 10-fold or greater selectivity for inhibition of 5α-reductase type 1 over type 2. These results demonstrate the utility of the compounds of the instant invention for the treatment of hyperandrogenic conditions.

17

A compound referrred to herein as a 5α-reductase 2 inhibitor is a compound that shows inhibition of the 5α-reductase 2 isozyme in the above-described assay.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of treating an androgen-related condition selected from:
    (1) benign prostatic hyperplasia,
    (2) prostatitis, and
    (3) hematuria, consisting essentially of administering to a patient in need of such treatment a calcium channel blocker in combination with a 5α-reductase inhibitor.

2. The method according to claim 1 wherein the androgen-related condition is selected from:
    (1) benign prostatic hyperplasia, and
    (2) prostatitis.

3. The method according to claim 2 wherein the androgen-related condition is benign prostatic hyperplasia.

4. The method according to claim 1 wherein the 5α-reductase inhibitor is selected from:
    (1) a compound of structural formula (I):

I

![structure I]

wherein R is selected from:
    (a) C$_{1-10}$ alkyl, unsubstituted or substituted with one to three halogen substituents,
    (b) phenyl, unsubstituted or substituted with one to three substituents independently selected from halogen, methyl, and trifluoromethyl
    (c) benzyl, unsubstituted or substituted on the methylene or phenyl group with one to three substituents independently selected from halogen, methyl and trifluoro methyl;

18

(2)

(3)

(4)

(5)

or a pharmaceutically acceptable salt or ester thereof.

5. The method according to claim 4 wherein the 5α-reductase inhibitor is a compound of structural formula (I):

wherein R is selected from:

(a) unsubstituted $C_{1-10}$ alkyl, (b) phenyl unsubstituted or substituted with one or two trifluoromethyl substituents, and (c) benzyl, unsubstituted or substituted on the methylene with one or two trifluoromethyl substituents, or a pharmaceutically acceptable salt thereof.

6. The method according to claim 5 wherein R is selected from:

(a) t-butyl;

(b) 2,5-bis(trifluoromethyl)phenyl; and

(c)

7. The method according to claim 6 herein the 5α-reductase inhibitor is finasteride.

8. The method of claim 1 wherein the calcium channel blocker is selected from:

(1) a compound of formula (II):

wherein:

(a) $R^1$ is selected from $C_{1-6}$ alkyl- and $C_{1-6}$ alkyloxy-$C_{1-6}$ alkyl-;

(b) $R^2$ is selected from: $C_{1-6}$ alkyl-, $C_{1-6}$ alkyloxy-$C_{1-6}$ alkyl -, $N(R^4)_2$—$C_{1-6}$ alkyl-O—$C_{1-6}$ alkyl-, and aryl-$C_{1-6}$ alkyl-N($R^4$)—$C_{1-6}$ alkyl;

(c) $R^3$ is selected from hydrogen and hydroxy;

(d) $R^4$ is selected from hydrogen, methyl and ethyl;

(e) $R^5$ is selected from hydrogen and heterocyclo-$C_{1-3}$ alkyl;

(f) X is selected from —$NO_2$, trifluoromethyl, 1,1-difluoromethoxy, methoxy, and halogen; and (g) Y is selected from hydrogen and halogen;

(2) a compound of structural formula (III):

wherein:

(a) $R^6$ is selected from hydrogen, methoxy, hydroxy, and halogen;

(b) $R^7$ is selected from hydrogen, $C_{1-5}$ alkyl, saturated or unsaturated $C_{3-6}$ cycloalkyl, benzyl and phenyl; and (c) $R^8$ is cyano; or alternatively, $R^7$ and $R^8$ may together form the following: —$SO_2(CH_2)_3SO_2$—;

(3) a compound of structural formula (VI):

wherein:

$R^{14}$ is selected from phenyl and benzyl;

(4) a compound of structural formula (IV):

wherein:

(a) $R^9$ is a phenyl group either unsubstituted or substituted with 1 to 3 substituents independently selected from $C_{1-8}$ alkyl, $C_{1-8}$ alkyloxy, and halogen;

(b) $R^{10}$ is selected from hydrogen and $C_{2-8}$ alkanoyl;

(c) $R^{11}$ and $R^{12}$ are each independently selected from $C_{1-8}$ alkyl;

(d) $X^1$ is selected from hydrogen and halogen; and (e) $Y^1$ is an alkylene group of 2 or 3 carbon atoms; and (5) a compound of structural formula (V):

(V)

wherein:
R$^{13}$ is independently selected from hydrogen and halogen at each occurrence;
or a pharmaceutically acceptable salt thereof.

9. The method according to claim 8, wherein:
R$^1$ is selected from:
(a) C$_{1-3}$ alkyl, and
(b) C$_{1-6}$ alkyloxy-C$_{1-2}$ alkyl-;
R$^2$ is selected from:
(a) C$_{1-4}$ alkyl,
(b) C$_{1-6}$ alkyloxy-C$_{1-2}$ alkyl-, and
(c) phenyl-C$_{1-2}$ alkyl-N(R$^4$)—C$_{1-6}$ alkyl;
R$^4$ is methyl;
R$^5$ is selected from:
(a) hydrogen, and
(b) 2-(4-morpholinyl)-ethyl-;
X is selected from:
(a) —NO$_2$,
(b) 1,1-difluoromethoxy, and
(c) chloro;
Y is selected from:
(a) hydrogen, and
(b) chloro;
R$^6$ is selected from:
(a) hydrogen, and
(b) methoxy,
R$^7$ is isopropyl;
R$^9$ is a phenyl group either unsubstituted or substituted with 1 to 3 substituents selected from:
(a) methyl,
(b) ethyl,
(c) propyl,
(d) isopropyl,
(e) butyl,
(f) methoxy,
(g) ethoxy,
(h) propoxy,
(i) isopropoxy, and
(j) butoxy;
R$^{10}$ is selected from:
(a) hydrogen,
(b) acetyl,
(c) propionyl, and
(d) butyryl;
R$^{11}$ and R$^{12}$ are independently selected from:
(a) methyl,
(b) ethyl,
(c) propyl,
(d) isopropyl, and
(e) butyl;
X$^1$ is selected from:
(a) hydrogen,
(b) chloro-, and
(c) bromo;
Y$^1$ is —CH$_2$—CH$_2$—; and
R$^{13}$ selected from:
(a) hydrogen, and
(b) fluorine.

10. The method according to claim 9, wherein:
R$^1$ is selected from:
(a) methyl,
(b) ethyl,
(c) isopropyl,
(d) isobutyl, and
(e) n-propyloxyethyl-;
R$^5$ is hydrogen;
X is selected from;
(a) —NO$_2$, and
(b) chloro;
Y is hydrogen;
R$^9$ is phenyl, either unsubstituted or substituted with a substituent selected from:
(a) methyl,
(b) methoxy, and
(c) chloro;
R$^{10}$ is selected from:
(a) acetyl, and
(b) hydrogen;
R$^{11}$ and R$^{12}$ are each methyl; and
X$^1$ is hydrogen.

11. The method of claim 1 wherein the calcium channel blocker is selected from:
(1) Nifedipine,
(2) Nicardipine,
(3) Nitrendipine,
(4) Nisoldipine,
(5) Felodipine,
(6) Nimodipine,
(7) Niludipine,
(8) Amlodipine,
(9) Flordipine,
(10) Ryosidine,
(11) FR 7534,
(12) Nilvadipine,
(13) PY 108-068,
(14) Isradipine,
(15) Verapamil,
(16) Gallopamil,
(17) Prenylamine,
(18) Fendiline,
(19) Terodiline,
(20) Bepridil,
(21) Terbutaline,
(22) Amiloride,
(23) Bencyclane,
(24) Etafenone,
(25) Diltiazern,
(26) Flunarizine, (27) Cinnarizine,
(28) Lidoflazine,
(29) Perhexiline, and
(30) Mibefradil.

12. The method of claim 11 wherein the calcium channel blocker is selected from:
(1) Nifedipine,
(2) Nicardipine,
(3) Nitrendipine,
(4) Nisoldipine,
(5) Felodipine,
(6) Nimodipine,
(7) Verapamil,
(8) Gallopamil,
(9) Diltiazem,
(10) Mibefradil,
(11) Bepridil,
(12) Isradipine, and
(13) Amlodipine.

13. The method of claim 7 wherein the calcium channel blocker is selected from:
(1) Nifedipine,
(2) Nicardipine,
(3) Nitrendipine,
(4) Nisoldipine,
(5) Felodipine,
(6) Nimodipine,
(7) Niludipine,
(8) Amlodipine,
(9) Flordipine,
(10) Ryosidine,
(11) FR 7534,
(12) Nilvadipine,
(13) PY 108-068,
(14) Isradipine,
(15) Verapamil,
(16) Gallopamil,
(17) Prenylamine,
(18) Fendiline,
(19) Terodiline,
(20) Bepridil,
(21) Terbutaline,
(22) Amiloride,
(23) Bencyclane,
(24) Etafenone,
(25) Diltiazem,
(26) Flunarizine,
(27) Cinnarizine,
(28) Lidoflazine, and
(29) Perbexiline, and
(30) Mibefradil.

14. The method of claim 13 wherein the calcium channel blocker is selected from:
(1) Nifedipine,
(2) Nicardipine,
(3) Nitrendipine,
(4) Nisoldipine,
(5) Felodipine,
(6) Nimodipine,
(7) Verapamil,
(8) Gallopamil, and
(9) Diltiazem,
(10) Mibefradil,
(11) Bepridil,
(12) Isradipine, and
(13) Amlodipine.

15. A method of treating benign prostatic hyperplasia comprising ministering to a patient in need of such treatment a calcium channel blocker in combination with a 5α-reductase inhibitor, wherein:

the calcium channel blocker is selected from:
(1) Nifedipine,
(2) Nicardipine,
(3) Nitrendipine,
(4) Nisoldipine,
(5) Felodipine,
(6) Nimodipine,
(7) Niludipine,
(8) Amlodipine,
(9) Flordipine,
(10) Ryosidine,
(11) FR 7534,
(12) Nilvadipine,
(13) PY 108-068,
(14) Isradipine,
(15) Verapamil,
(16) Gallopamil,
(17) Prenylamine,
(18) Fendiline,
(19) Terodiline,
(20) Bepridil,
(21) Terbutaline,
(22) Amiloride,
(23) Bencyclane,
(24) Etafenone,
(25) Diltiazem,
(26) Flunarizine,
(27) Cinnarizine,
(28) Lidoflazine,
(29) Perhexiline, and
(30) Mibefradil; and the 5α-reductase inhibitor is compound of structural formula (I):

wherein R is selected from:
(a) unsubstituted $C_{1-10}$ alkyl,
(b) phenyl unsubstituted or substituted with one or two trifluoromethyl substituents, and (c) benzyl, unsubstituted or substituted on the methylene with one or two trifluoromethyl substituents.

16. The method according to claim 15, wherein:
the calcium channel blocker is selected from:
   (1) Nifedipine,
   (2) Nicardipine,
   (3) Nisoldipine,
   (4) Felodipine,
   (5) Nimodipine,
   (6) Verapamil,
   (7) Diltiazem,
   (8) Mibefradil,
   (9) Bepridil,
   (10) Isradipine, and
   (11) Amlodipine; and
the 5α-reductase inhibitor is finasteride.

17. The method according to claim 16 wherein the calcium channel blocker and the 5α-reductase inhibitor are administered orally.

18. A composition consisting essentially of a pharmaceutically acceptable carrier and a therapeutically effective amount of a calcium channel blocker in combination with a therapeutically effective amount of a 5α-reductase inhibitor.

19. The composition according to claim 18 which is adapted for oral administration.

* * * * *

UNITED STATES PATENT AND TRADEMARK OFFICE
CERTIFICATE OF CORRECTION

Page 1 of 1

PATENT NO. : 6,268,377 B1
DATED : July 31, 2001
INVENTOR(S) : Joanne Waldstreicher, Daniel Z. Wang

It is certified that error appears in the above-identified patent and that said Letters Patent is hereby corrected as shown below:

Column 22, claim 11,
Line 66, "(25) Ditiazern" should be -- (25) Diltiazem --.

Signed and Sealed this

Fifteenth Day of January, 2002

Attest:

Attesting Officer

JAMES E. ROGAN
Director of the United States Patent and Trademark Office